US012551648B2

(12) United States Patent
Grashow et al.

(10) Patent No.: US 12,551,648 B2
(45) Date of Patent: Feb. 17, 2026

(54) EXHAUST ARRANGEMENT FOR PATIENT INTERFACE DEVICE AND PATIENT INTERFACE INCLUDING SAME

(71) Applicant: KONINKLIJKE PHILIPS N.V., Eindhoven (NL)

(72) Inventors: Jonathan Sayer Grashow, Monroeville, PA (US); Elizabeth Powell Margaria, Monroeville, PA (US); Robert Edward O'Grady, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 906 days.

(21) Appl. No.: 17/484,256

(22) Filed: Sep. 24, 2021

(65) Prior Publication Data

US 2022/0096768 A1 Mar. 31, 2022

Related U.S. Application Data

(60) Provisional application No. 63/085,436, filed on Sep. 30, 2020.

(51) Int. Cl.
*A61M 16/06* (2006.01)
*A61M 16/00* (2006.01)

(52) U.S. Cl.
CPC ........ *A61M 16/06* (2013.01); *A61M 16/0057* (2013.01); *A61M 2207/00* (2013.01)

(58) Field of Classification Search
CPC ............ A61M 16/0057; A61M 16/009; A61M 16/06; A61M 16/0627; A61M 16/0666;
(Continued)

(56) References Cited

U.S. PATENT DOCUMENTS 8,757,156 B2 6/2014 Domroese
8,851,075 B2 10/2014 Ng
(Continued)

FOREIGN PATENT DOCUMENTS

CN 105413078 A 3/2016
TW M585633 * 11/2019 ............ A61M 16/06
(Continued)

OTHER PUBLICATIONS

International Search Report for PCT/EP2021/076025 filed Sep. 22, 2021.

*Primary Examiner* — Margaret M Luarca
(74) *Attorney, Agent, or Firm* — Michael W. Haas

(57) ABSTRACT

An arrangement for exhausting gases from a cavity of a patient interface to an ambient environment, patient interface for use in providing a flow of treatment gas to the airway of a patient. The arrangement includes a body member that forms a portion of the patient interface between the cavity and the ambient environment. The body member includes: a number of inlets defined in a first side of the body member for receiving gases from the cavity; a number of outlets defined in a second side of the body member opposite the first side for provide for the exit of gases from the patient interface to the surrounding environment; and a number of high-drag passages defined in the body member extending laterally between an inlet of the number of inlets and an outlet of the number of outlets.

12 Claims, 8 Drawing Sheets

(58) Field of Classification Search
CPC .......... A61M 2207/00; A61M 2205/42; A61M 16/0816; A61M 2202/0085; A61M 16/208; A62B 18/00
See application file for complete search history.

(56) References Cited

U.S. PATENT DOCUMENTS

| | | | | |
|---|---|---|---|---|
| 10,272,218 | B2 * | 4/2019 | McAuley | A61M 16/0683 |
| 10,328,222 | B2 * | 6/2019 | Foote | A61M 16/0875 |
| 10,765,824 | B2 * | 9/2020 | Lee | A61M 16/06 |
| 10,980,958 | B2 * | 4/2021 | Ewers | A61M 16/06 |
| 11,883,597 | B2 * | 1/2024 | Eifler | A61M 16/06 |
| 2004/0094157 | A1 * | 5/2004 | Dantanarayana | A61M 16/0875 128/207.12 |
| 2009/0050156 | A1 * | 2/2009 | Ng | A61M 16/0816 128/205.24 |
| 2010/0051034 | A1 * | 3/2010 | Howard | A61M 16/0816 128/207.11 |
| 2014/0283831 | A1 | 9/2014 | Foote | |
| 2019/0091430 | A1 * | 3/2019 | Barlow | A61M 16/0611 |
| 2019/0209804 | A1 | 7/2019 | Dantanarayana | |
| 2019/0226799 | A1 | 7/2019 | Daley | |
| 2019/0262568 | A1 | 8/2019 | Chow | |
| 2020/0009345 | A1 | 1/2020 | Barbara | |
| 2020/0061326 | A1 | 2/2020 | Arrowsmith | |

FOREIGN PATENT DOCUMENTS

| | | | | |
|---|---|---|---|---|
| WO | WO-2018053589 A1 * | 3/2018 | | A61M 16/0816 |
| WO | WO-2018085889 A1 * | 5/2018 | | A61B 5/4818 |
| WO | WO-2020111951 A1 * | 6/2020 | | A61M 16/06 |

* cited by examiner

EXHAUST ARRANGEMENT FOR PATIENT INTERFACE DEVICE AND PATIENT INTERFACE INCLUDING SAME

CROSS-REFERENCE TO RELATED APPLICATIONS

This patent application claims the priority benefit under 35 U.S.C. § 119(e) of U.S. Provisional Application No. 63/085,436, filed on Sep. 30, 2020, the contents of which are herein incorporated by reference.

BACKGROUND OF THE INVENTION

1. Field of the Invention

The present invention pertains to patient interfaces for use in delivering a flow of a breathing gas to an airway of a patient. More particularly, the present invention pertains to exhaust arrangements for use in such patient interfaces. The present invention further pertains to a method of cleaning an exhaust arrangement utilized in patient interface.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interfaces may also employ other patient contacting components, such as forehead supports, cheek pads and chin pads. The patient interface is typically secured to the patient's head by a headgear component. The patient interface is connected to a gas delivery tube or conduit and interfaces the pressure support device with the airway of the patient, so that a flow of breathing gas can be delivered from the pressure/flow generating device to the airway of the patient via the patient interface. An exhaust port (also referred to as an exhalation vent, exhalation port, and/or exhaust vent) is provided in the gas delivery tube or conduit and/or the patient interface device to allow exhaust gas, such as the exhaled gas from the patient, to vent to atmosphere.

Typical exhaust ports comprise a single orifice (e.g. a slot) or an array of smaller holes which extend directly from the interior of the patient interface and/or tube/conduit via the shortest path (i.e., generally perpendicular to the wall of the patient interface and/or tube/conduit) to the surrounding environment. Common complaints for such type of exhaust port are that the exhausted air blows onto the patient (e.g. hits the patient's hands) or a patient's bed partner resulting in an uncomfortable feeling. Some newer exhaust port designs have tried to reduce such air jetting by using a mesh material or by covering the exhaust port hole(s) with a fiber material to attempt to diffuse the exhausted air. A common complaint with such mesh/fiber approaches is that they are difficult for a patient to keep clean and may provide a place for germs to grow as they are difficult or impossible to clean.

SUMMARY OF THE INVENTION

As one aspect of the present invention an arrangement structured to provide for the passage of gases from a cavity of a patient interface to an ambient environment in which patient interface is disposed, the patient interface being for use in providing a flow of a treatment gas to the airway of a patient, comprises: a body member sized and configured to form a portion of the patient interface between the cavity and the ambient environment, the body member comprising: a number of inlets defined in a first side of the body member, each inlet being positioned and structured to receive gases from the cavity; a number of outlets defined in a second side of the body member opposite the first side, each outlet being positioned and structured to provide for the exit of gases from the patient interface to the surrounding environment; and a number of high-drag passages defined in the body member, each high-drag passage extending laterally between an inlet of the number of inlets and an outlet of the number of outlets.

The number of high-drag passages may comprise a plurality of high-drag passages extending from one inlet of the number of inlets.

The one inlet may be in the shape of an elongated slot.

The body member may comprise an internal member and an external member coupled to the internal member, wherein the number of inlets are defined in the internal member, and wherein the number of outlets are defined in the external member.

The number of high-drag passages may be defined by a corresponding number of grooves formed in one or both of the internal member and/or the external member.

The number of high-drag passages may be defined by a corresponding number of grooves formed in the external member that are each bounded by a portion of the internal member thus defining each high-drag passage.

The number of grooves may be formed via one of: injection molding, machining, or 3D printing.

The external member may be selectively coupled to the internal member.

The internal member may comprise a portion of the patient interface.

Each high-drag passage may comprise at least one of: a number of textured surfaces, multiple bends, a length of at least 20 mm, and/or a minor diameter of 0.8 mm or less.

As another aspect of the present invention a patient interface for use in providing a flow of a treatment gas to the airway of a patient comprises: a body that defines a cavity therein that is structured to receive the flow of treatment gas; a first aperture defined therein that is positioned and structured to communicate the flow of treatment gas from the cavity to the airway of the patient; a sealing element disposed thereabout the first aperture, the sealing element being structured to sealingly engage about one or more of the nares and/or mouth of the patient; and an arrangement structured to provide for the passage of gases from the cavity to an ambient environment in which the patient interface is disposed, the arrangement comprising: a body member sized and configured to form a portion of the patient interface between the cavity and the ambient environment, the body member of the arrangement comprising: a number of inlets defined in a first side, each inlet being positioned and structured to receive gases from the cavity; a number of outlets defined in a second side opposite the first side, each outlet being positioned and structured to provide for the exit of gases from the patient interface to the ambient environment; and a number of high-drag passages defined in the body member of the arrangement, each high-drag passage extending laterally between an inlet of the number of inlets and an outlet of the number of outlets.

The body member of the arrangement may comprise an internal member and an external member coupled to the internal member, wherein the number of inlets are defined in the internal member, and wherein the number of outlets are defined in the external member.

Each high-drag passage may comprise at least one of: a number of textured surfaces, multiple bends, a length of at least 20 mm, and/or a minor diameter of 0.8 mm or less.

As yet a further aspect, a respiratory interface system for use in providing a regimen of respiratory therapy to a patient comprises: a pressure generating device structured to provide a flow of a treatment gas; a patient interface structured communicate the flow of treatment gas to an airway of the patient; and a delivery conduit coupled between the pressure generating device and the patient interface, the delivery conduit structured to communicate the flow of the treatment gas from the pressure generating device to the patient interface, wherein the patient interface comprises: a body that defines a cavity therein that is structured to receive the flow of treatment gas received from the delivery conduit; a first aperture defined therein that is positioned and structured to communicate the flow of treatment gas from the cavity to the airway of the patient; a sealing element disposed thereabout the first aperture, the sealing element being structured to sealingly engage about one or more of the nares and/or mouth of the patient; and an arrangement structured to provide for the passage of gases from the cavity to an ambient environment in which the patient interface is disposed, the arrangement comprising: a body member sized and configured to form a portion of the patient interface between the cavity and the ambient environment, the body member of the arrangement comprising: a number of inlets defined in a first side, each inlet being positioned and structured to receive gases from the cavity; a number of outlets defined in a second side opposite the first side, each outlet being positioned and structured to provide for the exit of gases from the patient interface to the ambient environment; and a number of high-drag passages defined in the body member of the arrangement, each high-drag passage extending laterally between an inlet of the number of inlets and an outlet of the number of outlets.

Each high-drag passage may comprise at least one of: a number of textured surfaces, multiple bends, a length of at least 20 mm, and/or a minor diameter of 0.8 mm or less.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
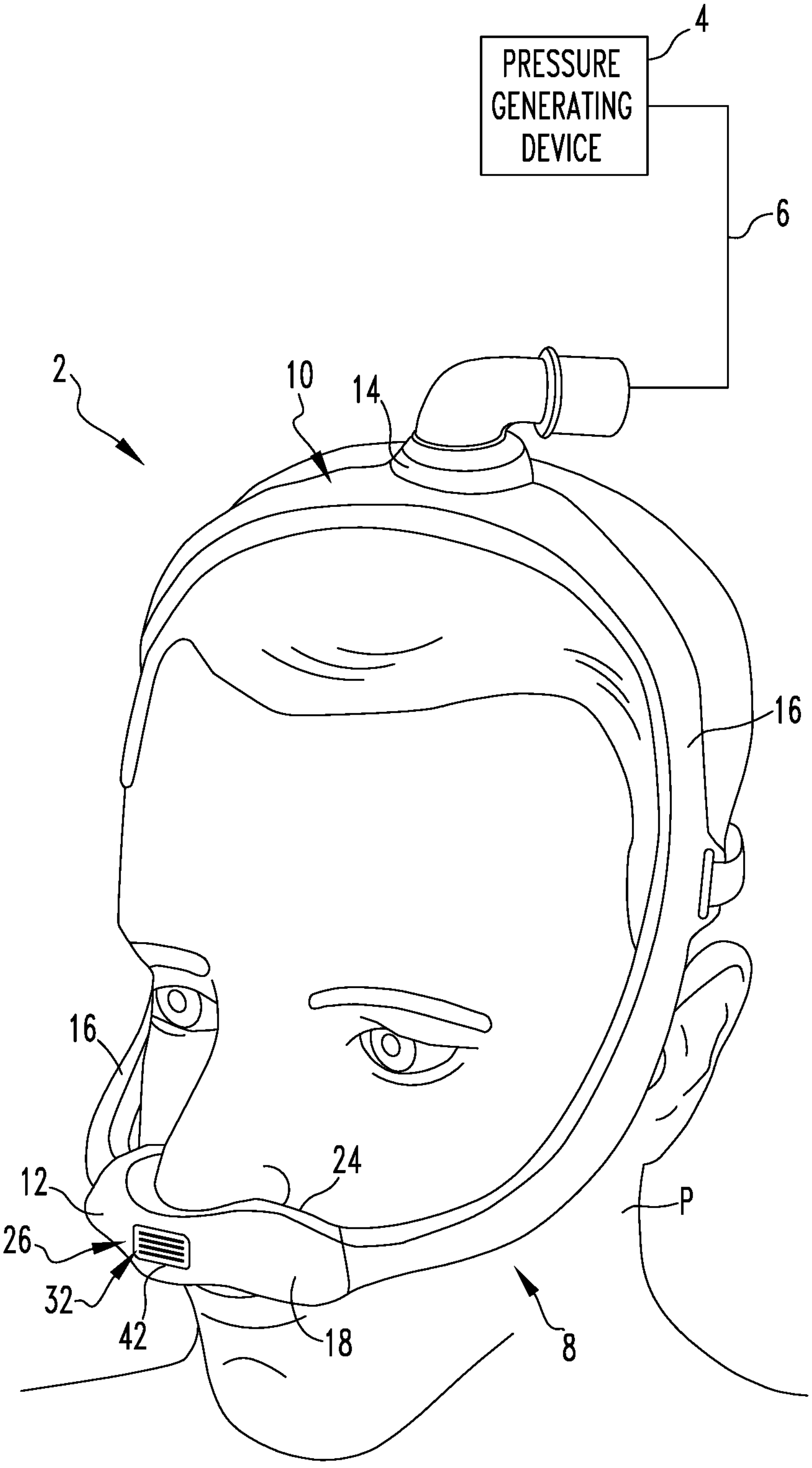
FIG. 1 is a partially schematic depiction of a respiratory interface system for use in providing a flow of positive pressure breathing gas to the airway of a patient including an arrangement for providing for the passage of gases from a cavity of the patient interface in accordance with one example embodiment of the present invention, shown with a patient interface thereof disposed on the head of a patient.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the statement that two or more parts or components "engage" one another shall means that the parts exert a force against one another either directly or through one or more intermediate parts or components.

As used herein, the word "unitary" means a component is created as a single piece or unit. That is, a component that includes pieces that are created separately and then coupled together as a unit is not a "unitary" component or body.

As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such the components of a "coupling assembly" may not be described at the same time in the following description.

As used herein, a "coupling" is one element of a coupling assembly. That is, a coupling assembly includes at least two components, or coupling components, that are structured to be coupled together. It is understood that the elements of a coupling assembly are compatible with each other. For example, in a coupling assembly, if one coupling element is a snap socket, the other coupling element is a snap plug.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening is/are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein. That is, not so close as to cause substantial friction, as with a snug fit, but with more contact and friction than a "corresponding fit," i.e. a "slightly larger" fit.

A respiratory interface system 2 adapted to provide a regimen of respiratory therapy to a patient P according to one exemplary embodiment of the present invention is shown in FIG. 1. Respiratory interface system 2 includes a pressure generating device 4 (shown schematically), and a delivery conduit 6 (shown schematically) fluidly coupled to a mask 8. Pressure generating device 4 is structured to generate a flow of positive pressure breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, PA), and auto-titration pressure support devices. Delivery conduit 6 is structured to communicate the flow of breathing gas from pressure generating device 4 to mask 8, and mask 8 is structured to further communicate the flow of breathing gas received from conduit 6 to an airway of patient P. Delivery conduit 6 and mask 8 are often collectively referred to as a patient circuit.

Figure 2:
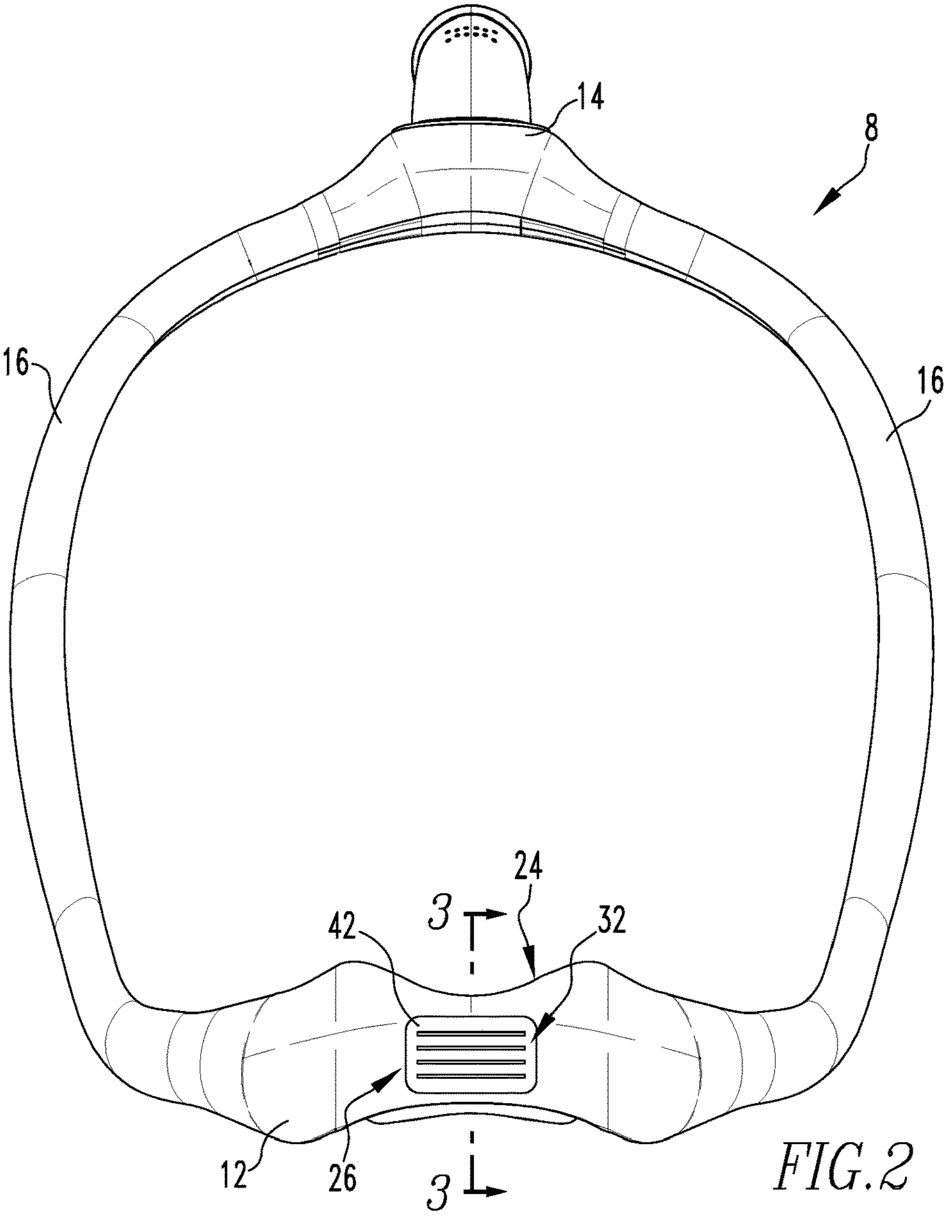
FIG. 2 is a front elevation view of the patient interface of FIG. 1.

Continuing to refer to FIG. 1, as well as to FIG. 2, mask 8 includes a tubing assembly 10 and a patient interface 12 coupled to tubing assembly 10. Tubing assembly 10 includes a manifold portion 14 structured to receive the flow of positive pressure breathing gas from delivery conduit 6, a number (two are shown in the example of FIGS. 1 and 2) of tubular portions 16 which each extend from manifold portion 14 to a distal end (not numbered) which is selectively coupled to patient interface 12. It is to be appreciated that other arrangements aside from tubing assembly 10 may be employed in mask 8 to provide the flow of positive pressure breathing gas produced by pressure generating device 4 to patient interface 12 without varying from the scope of the present invention.

Figure 3:
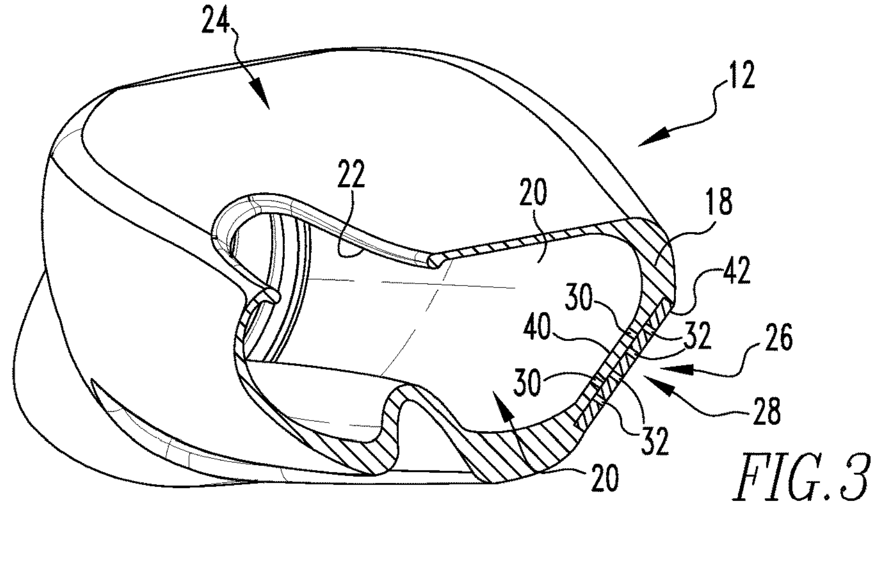
FIG. 3 is a section view of the patient interface of FIGS. 1 and 2 taken along line 3-3 of FIG. 2.
Figure 4:
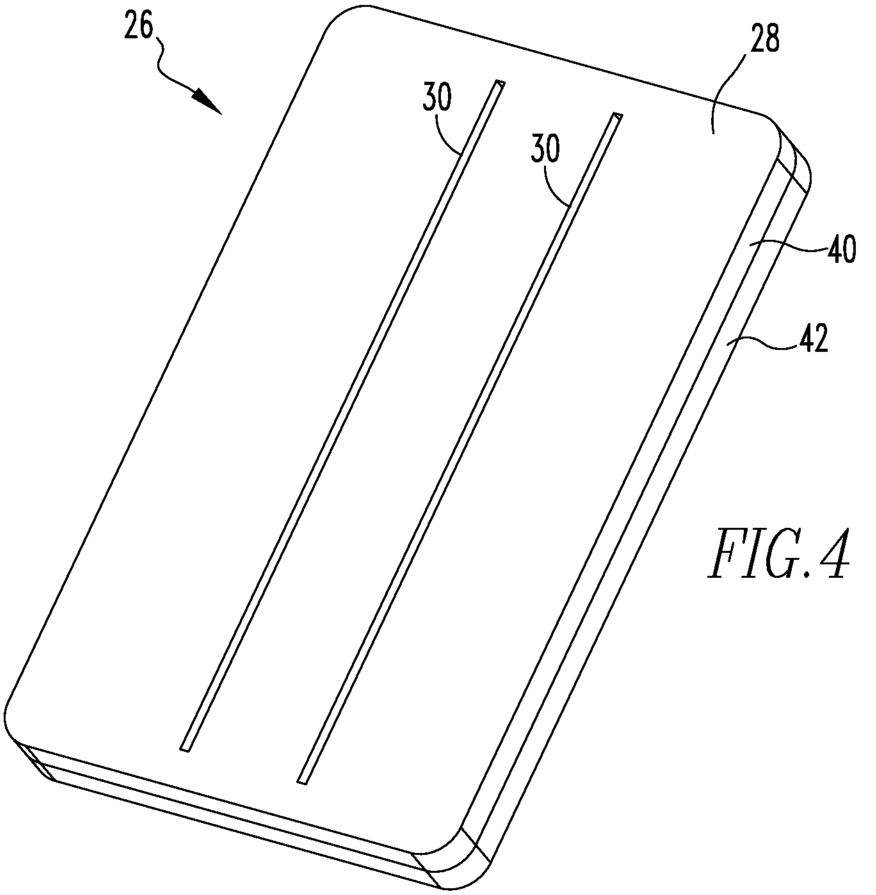
FIG. 4 is a perspective view of an inlet side of another arrangement for providing for the passage of gases from a cavity of a patient interface to an ambient environment in accordance with one example embodiment of the present invention.
Figure 5:
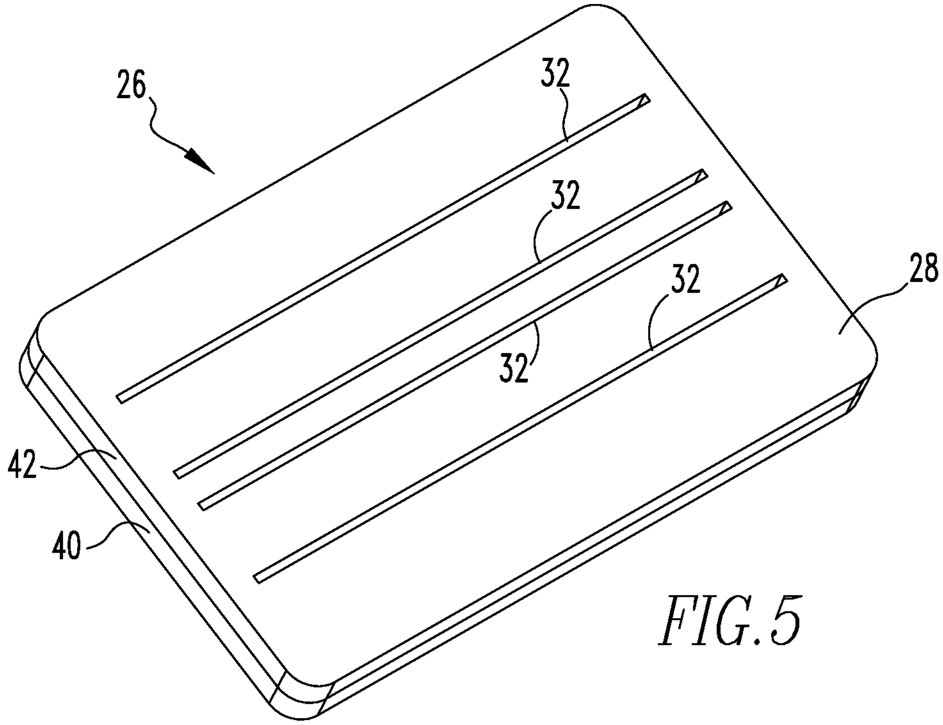
FIG. 5 is a perspective view of the opposite, outlet side of the arrangement of FIG. 4.
Figure 6:
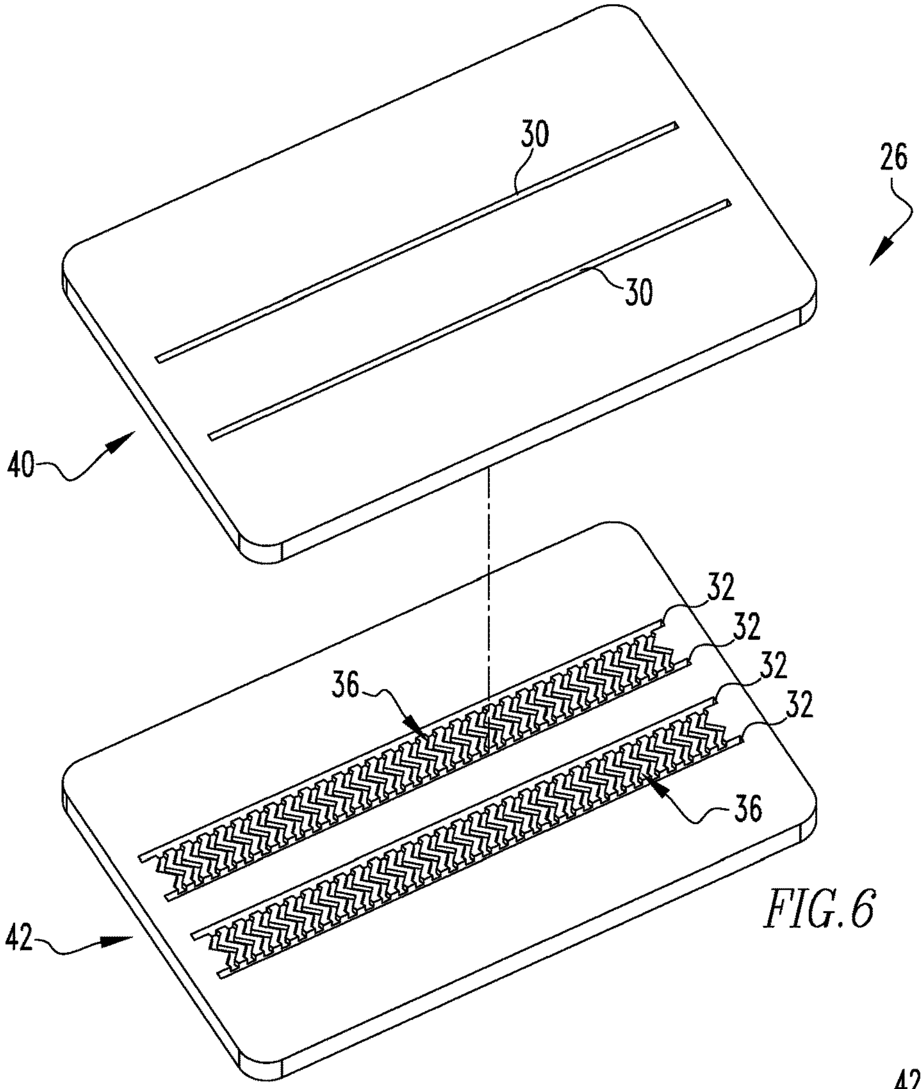
FIG. 6 is an exploded view of the arrangement of FIGS. 4 and 5.
Figure 7:
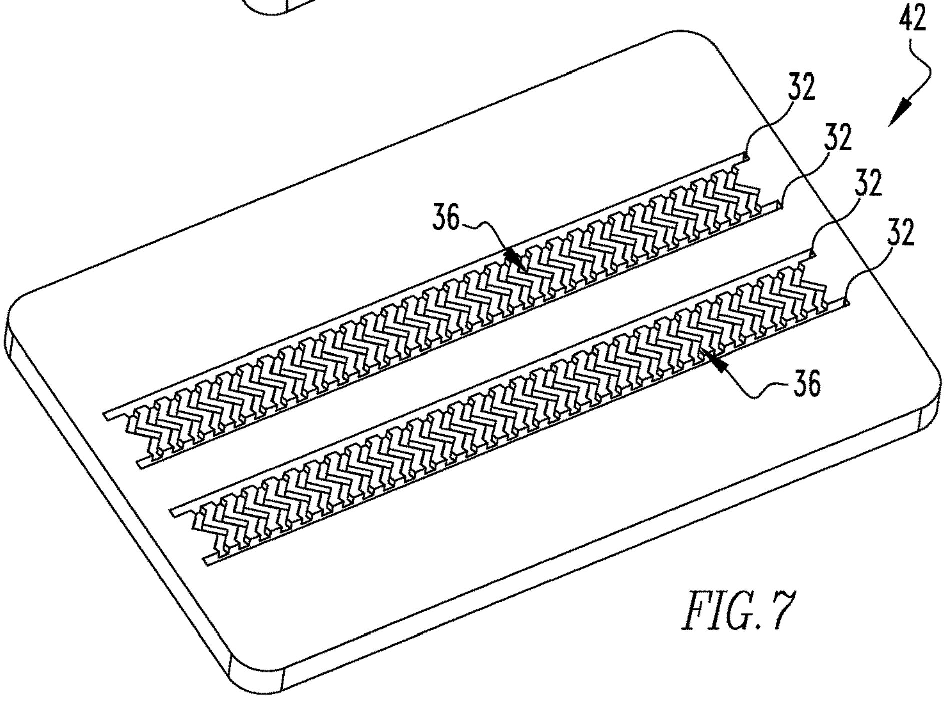
FIG. 7 is a perspective view of an internal face of an external member of the arrangement of FIGS. 4-6.
Figure 8:
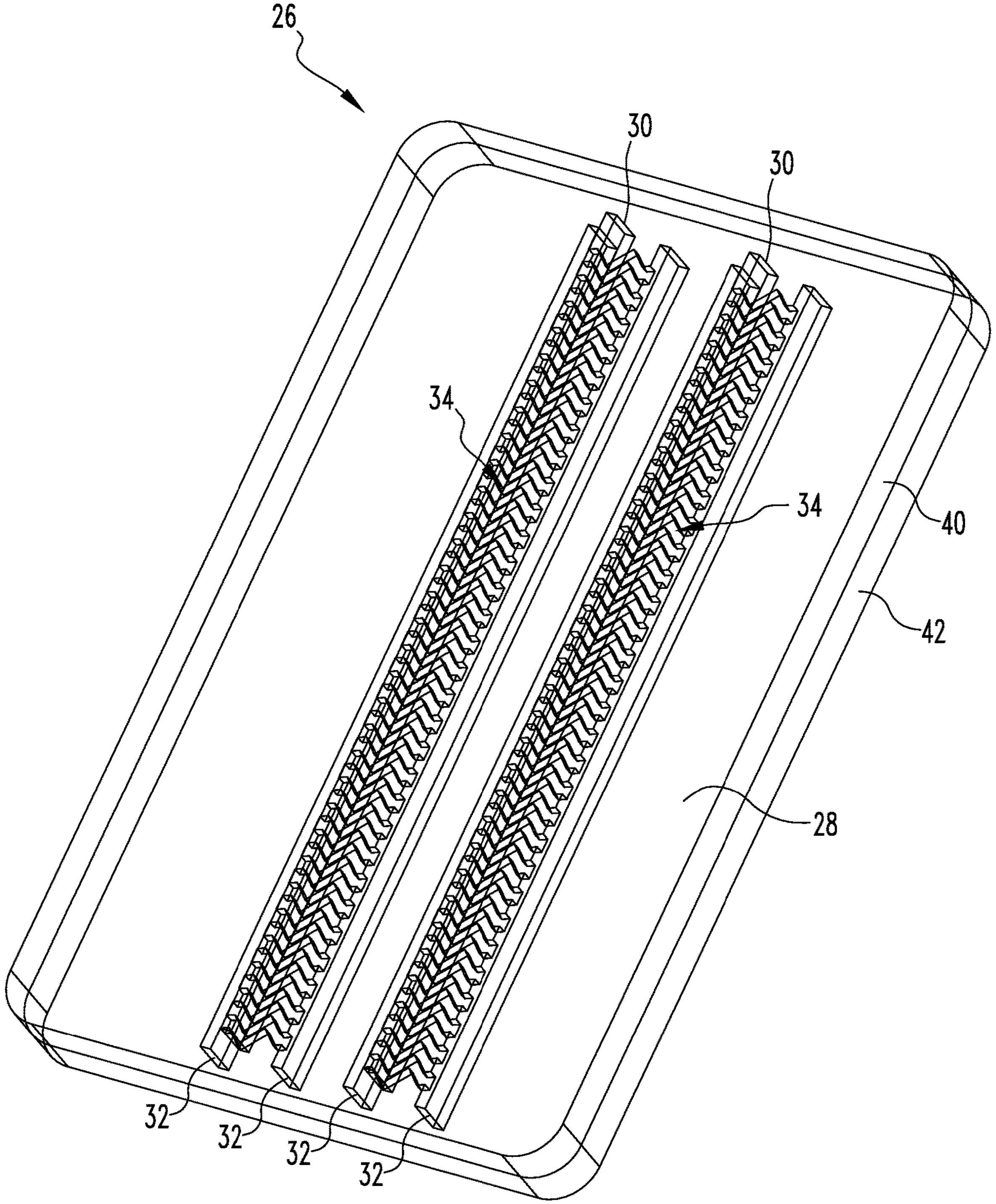
FIG. 8 is another perspective view of the inlet side of the arrangement of FIGS. 4-6 shown generally transparent in order to show details of internal structures thereof.

Referring now to FIG. 3, in addition to FIGS. 1 and 2, patient interface 12 includes a body 18 that defines a cavity 20 therein that is structured to receive (e.g., via tubing assembly 10) the flow of positive pressure breathing gas produced by pressure generating device 4. In the one example shown in FIGS. 1-3, body 18 is made of a soft, flexible material, such as, without limitation, silicone, an appropriately soft thermoplastic elastomer, a closed-cell foam, or any other suitable material or combination of such materials, however, it is to be appreciated that body 18 may be formed from one or more other suitable materials without varying from the scope of the present invention. Patient interface 12 further includes a first aperture 22 defined therein that is positioned and structured to communicate the flow of breathing gas from cavity 20 to the airway of the patient and a sealing element 24 disposed thereabout first aperture 22 which is structured to sealingly engage about one or more of the nares and/or mouth of patient P (depending on the particular patient interface arrangement).

In the example embodiment illustrated in FIGS. 1-3, sealing element 24 is formed as an integral portion of body 18, and thus is made of a soft, flexible material, such as, without limitation, silicone, an appropriately soft thermoplastic elastomer, a closed-cell foam, or any other suitable material or combination of such materials. It is to be appreciated, however, that sealing element 24 may be formed as a separate element and may take the form of any type of patient sealing element, such as a nasal/oral mask, a nasal pillow or a full face mask, which facilitates the delivery of the flow of breathing gas to the airway of a patient, without varying from the scope of the present invention. Patient interface 12 further includes an arrangement 26 coupled to, or provided in-part as a portion of, body 18 that provides for the passage of gases (e.g., patient exhalation gases) from cavity 20 of patient interface 12 to an ambient environment in which body 18, and thus patient interface 12, is disposed.

Referring now to FIGS. 4-8, in addition to FIGS. 1-3, arrangement 26 includes a generally thin, plate-like body member 28 formed from a plastic or other suitable rigid or semi-rigid material (e.g., metal, elastomer, etc.) that is sized and configured to form a portion of patient interface 12 between cavity 20 and the ambient environment in which the patient interface is disposed. Body member 28 includes a number of inlets 30 defined in an inlet side thereof, with each inlet 30 being positioned and structured to receive gases from cavity 20. In the example shown in FIGS. 4-8, two inlets 30 generally shaped as elongated slots are provided, however, it is to be appreciated that either or both of the quantity and/or shape of number inlets 30 may be varied without varying from the scope of the present invention. Body member 28 further includes a number of outlets 32 defined in an outlet side thereof, opposite the inlet side, with each outlet 32 being positioned and structured to provide for the exit of gases from arrangement 26, and thus patient interface 12, to the ambient environment. In the example shown in FIGS. 4-8, four outlets 32 generally shaped as elongated slots are provided, however, it is to be appreciated that either or both of the quantity and/or shape of number outlets 32 may be varied without varying form the scope of the present invention.

Body member 28 also includes a number of high-drag passages 34 defined therein, with each high-drag passage extending laterally (i.e., within body member 28 generally parallel to outer surfaces thereof and/or perpendicular to a straight through passage) a distance between an inlet 30 of the number of inlets 30 and an outlet 32 of the number of outlets 32. As used herein, a "high-drag passage" is a passage having walls dimensioned and/or positioned so as to slow the airflow velocity of gases passing therethrough without the use of a blocking material positioned therein. For example, a passage having a fibrous material disposed therein is not a "high-drag passage". As another example, a passage extending straight through a wall (i.e., perpendicular to the wall) is also not a "high-drag passage". In the example shown in FIGS. 4-8, each high-drag passage includes opposing sidewalls having 90 degree bends that act to slow the airflow velocity of gases passing therethrough. Other arrangements of high-drag passages may include, for example, without limitation, one or more of: textured surfaces, multiple bends, long/narrow passages (e.g., passages having a length of 20 mm or more, passages having a minor diameter (i.e., the smaller dimension of an elliptical or rectangular channel cross-section) of 0.2 mm to 8 mm. The example shown in FIGS. 4-8 includes a plurality of high-drag passages 34 (FIG. 8) extending between each inlet 30 and outlet 32. However, it is to be appreciated that the quantity of high-drag passages and/or the quantity of inlets and/or outlets in which they extend between may be varied without varying from the scope of the present invention.

As shown in the example embodiment of FIGS. 4-8, body member 28 may be formed from a generally thin, plate-like, internal member 40 structured to be positioned bounding cavity 20, and a generally thin, plate-like, external member 42 that is coupled to internal member 40 and positioned to be in communication with the ambient environment in which patient interface 12 is disposed. In such example embodiment the number of inlets 30 are defined in, and through internal member 40, while the number of outlets 32 are defined in and through external member. Also in such embodiment the number of high-drag passages 34 are defined in-part by a corresponding number of channels or grooves 36 (FIGS. 6 and 7) defined in external member 42 and, when external member 42 is coupled to internal member 40, by corresponding portions of internal member 40. Alternatively, the number of high-drag passages 34 may be similarly formed by channels or grooves defined in internal member 40 that interact with corresponding portions of external member 42 or by channels or grooves formed in both internal member 40 and external member 42 that interact with corresponding portions of the other member 40, 42 to define high-drag passages 34. As shown in the sectional view of FIG. 3, internal member 40 may be coupled to, or formed as an integral portion of, body 18 of patient interface 12. Alternatively, external member 42 may be coupled to, or formed as an integral portion of, body 18 of patient interface 12.

By relying on the geometry of mating surfaces of multiple components to create the enclosed high-drag passages 34, it is possible to create passages that otherwise could not be easily manufactured due to their small size, small diameter to length ratio, and/or torturous shape. The channels or grooves from which the high-drag passages are defined in-part may be formed from any suitable method such as, for example, without limitation, injection molding, machining, chemical etching, and/or 3D printing. In addition to providing for forming passages of complex geometries to be readily created, such modular construction additionally provides for the elements to be separated without damage if/when selectively coupled together (e.g., a snap fit, interference fit, or other suitable arrangement), thus exposing the channels that form each of the high-drag passages for cleaning thereof and/or replacement depending on the particular application.

Figure 9:
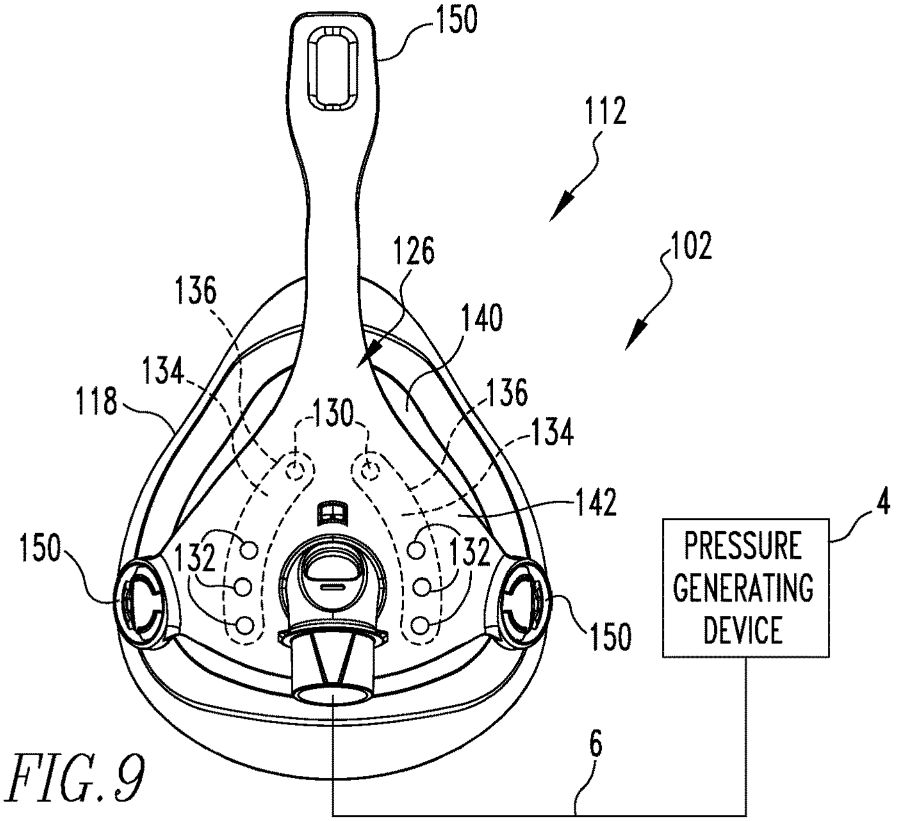
FIG. 9 is a partially schematic depiction of another respiratory interface system for use in providing a flow of positive pressure breathing gas to the airway of a patient having a patient interface, shown in front elevation, including another arrangement for providing for the passage of gases from a cavity of the patient interface in accordance with one example embodiment of the present invention.
Figure 10:
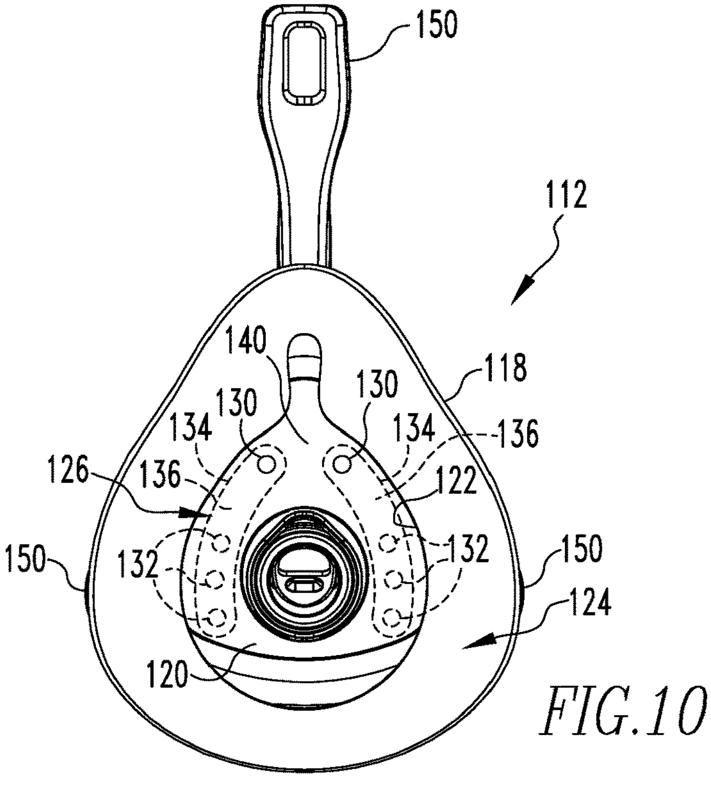
FIG. 10 is a rear elevation view of the patient interface of FIG. 9.
Figure 11:
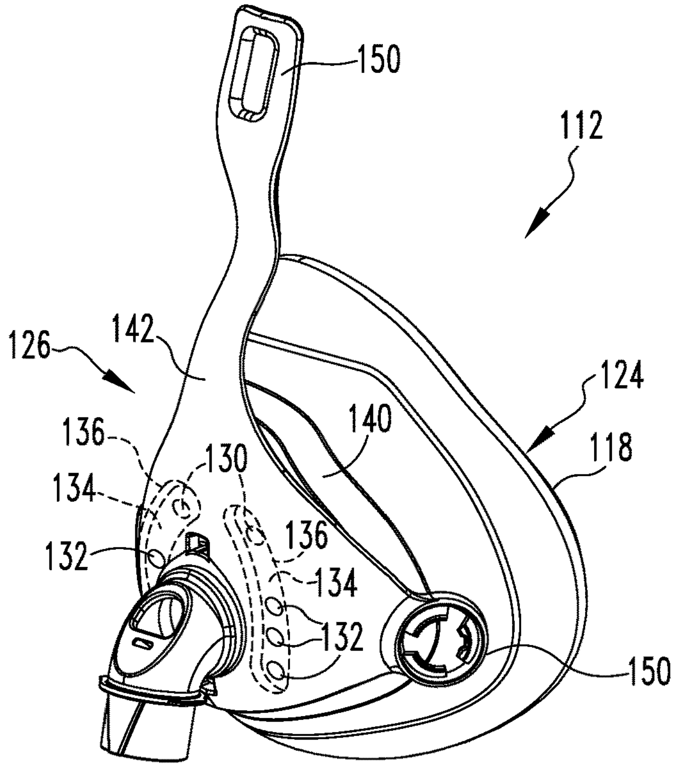
FIG. 11 is a front perspective view of the patient interface of FIGS. 9 and 10.
Figure 12:
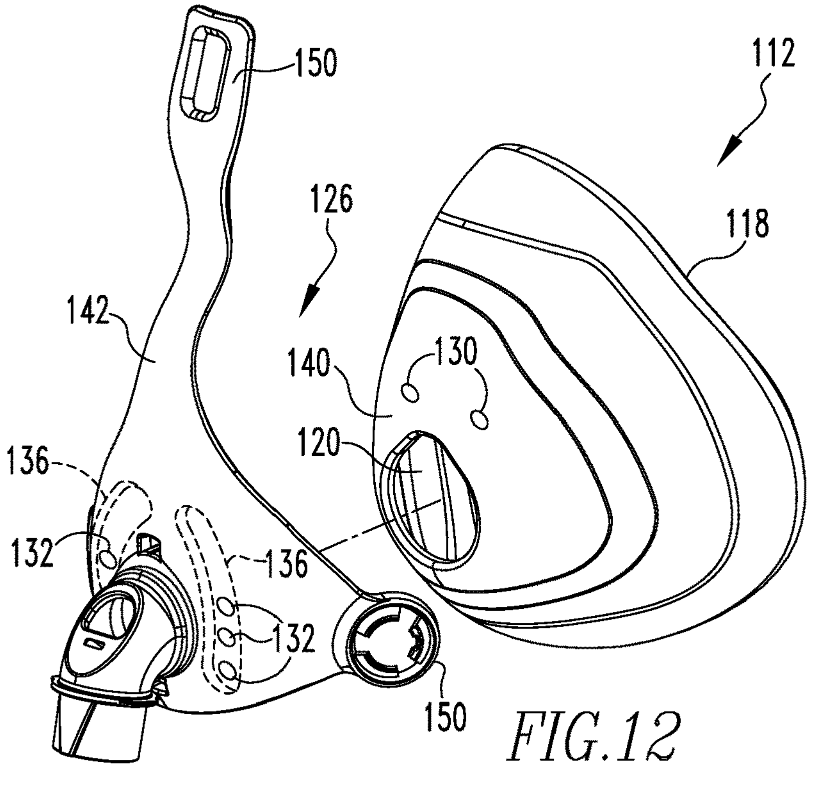
FIG. 12 is a front exploded perspective view of the patient interface of FIGS. 9-11.
Figure 13:
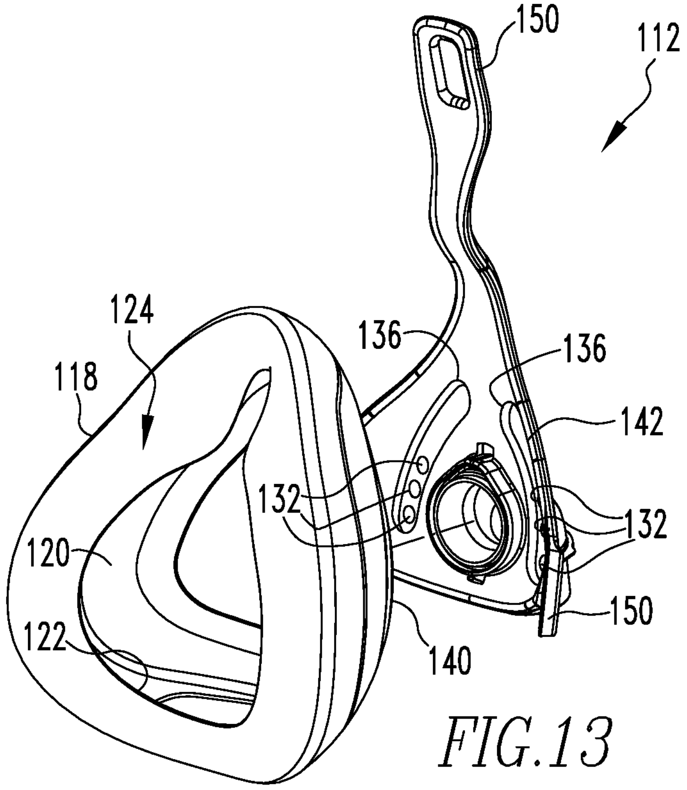
FIG. 13 is a rear exploded perspective view of the patient interface of FIGS. 9-11.

Another respiratory interface system 102 adapted to provide a regimen of respiratory therapy to a patient P according to another exemplary embodiment of the present invention is shown in FIG. 9. Like respiratory interface system 2 previously discussed, respiratory interface system 102 includes pressure generating device 4 (shown schematically) coupled, via conduit 6 (also shown schematically), to a patient interface 112 for providing the flow of positive pressure breathing gas thereto. Continuing to refer to FIG. 9, as well as to FIGS. 10-13, patient interface 112 includes a body 118 that defines a cavity 120 therein that is structured to receive (e.g., via conduit 6) the flow of positive pressure breathing gas produced by pressure generating device 4. In the one example shown in FIGS. 9-13, body 118 is made of a soft, flexible material, such as, without limitation, silicone, an appropriately soft thermoplastic elastomer, a closed-cell foam, or any other suitable material or combination of such materials, however, it is to be appreciated that body 118 may be formed from one or more other suitable materials without varying from the scope of the present invention. Patient interface 112 further includes a first aperture 122 defined therein that is positioned and structured to communicate the flow of breathing gas from cavity 120 to the airway of the patient and a sealing element 124 disposed thereabout first aperture 122 which is structured to sealingly engage about one or more of the nares and/or mouth of patient P (depending on the particular patient interface arrangement).

Patient interface 112 further includes an arrangement 126 coupled to, or provided in-part as a portion of, body 118 that provides for the passage of gases (e.g., patient exhalation gases) from cavity 120 of patient interface 12 to an ambient environment in which body 118, and thus patient interface 112, is disposed. Similar to arrangement 26 previously discussed, arrangement 126 includes a generally thin, plate-like, internal member in the form of a generally rigid faceplate 140 that is positioned bounding cavity 120 and generally surrounded by sealing element 124, and a generally thin, plate-like, external member in the form of a frame 142 that may be permanently or selectively coupled to faceplate 140 and positioned in communication with the ambient environment in which patient interface 112 is disposed. Frame 142 includes a number of securement points or structures 150 to which a suitable headgear or other stabilizing (e.g., a forehead support) and/or securement arrangement (not shown) may be coupled in order to secure/stabilize patient interface on the face/head of a patient. In such example embodiment, a number of inlets 130 are defined in, and through faceplate 140, while a number of outlets 132 (shown generally schematically enlarged in order to merely demonstrate their general positioning in the example embodiment) are defined in and through frame 142. Additionally in such embodiment, a number of high-drag passages 134 are defined in-part by a corresponding number of channels or grooves 136 defined in frame 142 and, when frame 142 is coupled to faceplate 140, by corresponding portions of faceplate 140. Alternatively, the number of high-drag passages 134 may be similarly formed by channels or grooves defined in faceplate 140 that interact with corresponding portions of frame 142 or by channels or grooves formed in both faceplate 140 and frame 142 that interact with corresponding portions of the other element 140, 142 to define high-drag passages 134.

The example arrangement 126 shown in FIGS. 9-13 includes high-drag passages 134, each with one circular inlet 130 and three circular outlets 132 associated therewith. It is to be appreciated, however, that such particular arrangement is shown for exemplary purposes only and that one or more of: the quantity, sizing, and/or layout of such high-drag passages 134; the quantity, sizing, and/or shape of the inlets 130; and the quantity, sizing, and/or shape of the outlets 132 may be varied without varying from the scope of the present invention.

From the foregoing examples it is to be appreciated that embodiments of the present invention provide arrangements for exhausting gases from a patient interface that improve upon known solutions. Such arrangements may include anywhere form a single large channel to an array of hundreds of channels depending on the particular application. When more channels are utilized, channels of shorter length and/or lesser cross-sectional area are needed. Accordingly, embodiments of the present invention can generally be tailored as needed to fit a particular patient interface arrangement.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. An arrangement structured to provide for the passage of gases from a cavity of a patient interface to an ambient environment in which the patient interface is disposed, the patient interface being for use in providing a flow of a treatment gas to the airway of a patient, the arrangement comprising:

a body member sized and configured to form a portion of the patient interface between the cavity and the ambient environment, the body member comprising:

(a) a first plate having a linear inlet passage defined therein through an entire thickness of the first plate, the linear inlet passage being positioned and structured to receive gases from the cavity;

(b) a second plate have a shape generally matching the first plate, wherein the first plate and the second plate are stacked on top of one another to form the body member, the second plate including:

a pair of linear outlets defined therein through and entire thickness of the second plate, wherein the pair of outlets disposed in parallel with each other and in parallel with the linear inlet passage responsive to the first plate and the second plate being stacked on top of one another, each outlet being positioned and structured to provide for the exit of gases from the patient interface to the ambient environment, wherein the linear inlet passage is disposed between the pair of outlets responsive to the first plate and the second plate being stacked on top of one another; and a plurality of passages defined in the second plate through a portion of a thickness of the second plate, each passage communicating with the linear inlet passage at a central portion of the passage and extending between the pair of outlets, wherein each passage in the plurality of passages spans between the pair of linear outlets in the second plate in a direction orthogonal to the pair of outlets in the second plate and orthogonal to the linear inlet passage in the first plate responsive to the first plate and the second plate being stacked on top of one another, and wherein each passage in the plurality of passages defines a tortuous path having a generally zig-zag shape between the linear inlet passage and each outlet in the pair of outlets.

2. The arrangement of claim 1, wherein the linear inlet passage is in the shape of an elongated slot.

3. The arrangement of claim 1, wherein the number of plurality of passages are defined by a corresponding number of grooves formed in one or both of the first plate and/or the second plate.

4. The arrangement of claim 1, wherein the plurality of passages are defined by a corresponding number of grooves formed in the second plate that are each bounded by a portion of the internal member thus defining each passage.

5. The arrangement of claim 4, wherein the number of grooves are formed via one of: injection molding, machining, etching, or 3D printing.

6. The arrangement of claim 4, wherein the external member is selectively coupled to the internal member.

7. The arrangement of claim 4, wherein the first member comprises a portion of the patient interface.

8. The arrangement of claim 1, wherein each passage comprises at least one of: a number of textured surfaces, multiple bends, a length of at least 20 mm, and/or a minor diameter of 0.8 mm or less.

9. A patient interface for use in providing a flow of a treatment gas to the airway of a patient, the patient interface comprising:

(a) a body that defines a cavity therein that is structured to receive the flow of treatment gas;

(b) a first aperture defined therein that is positioned and structured to communicate the flow of treatment gas from the cavity to the airway of the patient;

(c) a sealing element disposed thereabout the first aperture, the sealing element being structured to sealingly engage about one or more of the nares and/or mouth of the patient; and (d) an arrangement structured to provide for the passage of gases from the cavity to an ambient environment in which the patient interface is disposed, the arrangement comprising:

(1) a body member sized and configured to form a portion of the patient interface between the cavity and the ambient environment, the body member comprising:

(i) a first plate having a linear inlet passage defined therein through an entire thickness of the first plate, the linear inlet passage being positioned and structured to receive gases from the cavity;

(ii) a second plate have a shape generally matching the first plate, wherein the first plate and the second plate are stacked on top of one another to form the body member, the second plate including:

a pair of linear outlets defined therein through and entire thickness of the second plate, wherein the pair of outlets disposed in parallel with each other and in parallel with the linear inlet passage responsive to the first plate and the second plate being stacked on top of one another, each outlet being positioned and structured to provide for the exit of gases from the patient interface to the ambient environment, wherein the linear inlet passage is disposed between the pair of outlets responsive to the first plate and the second plate being stacked on top of one another; and a plurality of passages defined in the second plate through a portion of a thickness of the second plate, each passage communicating with the linear inlet passage at a central portion of the passage and extending between the pair of outlets, wherein each passage in the plurality of passages spans between the pair of linear outlets in the second plate in a direction orthogonal to the pair of outlets in the second plate and orthogonal to the linear inlet passage in the first plate responsive to the first plate and the second plate being stacked on top of one another, and wherein each passage in the plurality of passages defines a tortuous path having a generally zig-zag shape between the linear inlet passage and each outlet in the pair of outlets.

10. The patient interface of claim 9, wherein each passage comprises at least one of: a number of textured surfaces, multiple bends, a length of at least 20 mm, and/or a minor diameter of 0.8 mm or less.

11. A respiratory interface system for use in providing a regimen of respiratory therapy to a patient, the system comprising:

(a) a pressure generating device structured to provide a flow of a treatment gas;

(b) a patient interface structured communicate the flow of treatment gas to an airway of the patient; and (c) a delivery conduit coupled between the pressure generating device and the patient interface, the delivery conduit structured to communicate the flow of the treatment gas from the pressure generating device to the patient interface, wherein the patient interface comprises:

(1) a body that defines a cavity therein that is structured to receive the flow of treatment gas received from the delivery conduit;

(2) a first aperture defined therein that is positioned and structured to communicate the flow of treatment gas from the cavity to the airway of the patient;

(3) a sealing element disposed thereabout the first aperture, the sealing element being structured to sealingly engage about one or more of the nares and/or mouth of the patient; and (4) an arrangement structured to provide for the passage of gases from the cavity to an ambient environment in which the patient interface is disposed, the arrangement comprising:

(1) a body member sized and configured to form a portion of the patient interface between the cavity and the ambient environment, the body member comprising:

(i) a first plate having a linear inlet passage defined therein through an entire thickness of the first plate, the linear inlet passage being positioned and structured to receive gases from the cavity;

(ii) a second plate have a shape generally matching the first plate, wherein the first plate and the second plate are stacked on top of one another to form the body member, the second plate including:

a pair of linear outlets defined therein through and entire thickness of the second plate, wherein the pair of outlets disposed in parallel with each other and in parallel with the linear inlet passage responsive to the first plate and the second plate being stacked on top of one another, each outlet being positioned and structured to provide for the exit of gases from the patient interface to the ambient environment, wherein the linear inlet passage is disposed between the pair of outlets responsive to the first plate and the second plate being stacked on top of one another; and a plurality of passages defined in the second plate through a portion of a thickness of the second plate, each passage communicating with the linear inlet passage at a central portion of the passage and extending between the pair of outlets, wherein each passage in the plurality of passages spans between the pair of linear outlets in the second plate in a direction orthogonal to the pair of outlets in the second plate and orthogonal to the linear inlet passage in the first plate responsive to the first plate and the second plate being stacked on top of one another, and wherein each passage in the plurality of passages defines a tortuous path having a generally zig-zag shape between the linear inlet passage and each outlet in the pair of outlets.

12. The respiratory interface system of claim 11, wherein each passage comprises at least one of: a number of textured surfaces, multiple bends, a length of at least 20 mm, and/or a minor diameter of 0.8 mm or less.

* * * * *